United States Patent [19]

Mack et al.

[11] Plant 4,517

[45] Apr. 1, 1980

[54] CHRYSANTHEMUM PLANT

[75] Inventors: Grace H. Mack, 108 Wahackme Rd., New Canaan, Conn. 06840; Walter H. Jessel, Jr., Grantsville, W. Va.; William E. Duffett, Salinas, Calif.

[73] Assignee: Grace H. Mack, New Canaan, Conn.

[21] Appl. No.: 972,160

[22] Filed: Dec. 21, 1978

[51] Int. Cl.[2] ..... A01H 5/00

[52] U.S. Cl. ..... Plt./75

[58] Field of Search ..... Plt./75, 78

*Primary Examiner*—Robert E. Bagwill

*Attorney, Agent, or Firm*—Donald D. Jeffery

[57] ABSTRACT

A chrysanthemum cultivar particularly characterized as to uniqueness by the combined characteristics of flat capitulum form, pompon capitulum type, medium yellow ray floret color, diameter across face of capitulum up to 4 cm., short plant height, spreading branching pattern, average natural season flowering date of September 28, and average flowering response period of seven weeks in photoperiodic controlled short day programs.

1 Drawing Figure

The present invention comprises a new and distinct cultivar of *Chrysanthemum morifolium,* Ramat., hereinafter referred to by the cultivar name Westpoint.

Westpoint is a product of a planned breeding program which had the objective of creating cultivars with pompon capitulum type, short height, spreading branching pattern, durable inflorescence, short (six to seven week) flowering response period, and yellow ray floret color under outdoor natural season conditions.

Westpoint was originated from a cross made in a controlled breeding program in New Canaan, Conn. in the year 1970. The female parent was 940 (#21740E25; unnamed seedling). The male parent was Little Gem (unpatented; commercially available).

Westpoint was discovered and selected as a flowering plant within the progeny of the stated cross by Grace H. Mack and Walter H. Jessel, Jr. on Oct. 19, 1971 in an outdoor field in Barberton, Ohio. The first act of asexual reproduction of Westpoint was accomplished when vegetative cuttings were taken from the initial selection in February, 1972 by a technician working under formulations established and supervised by Walter H. Jessel, Jr. and William E. Duffett. Horticultural examination of selected units initiated June 5, 1972 has demonstrated that the combination of characteristics as herein disclosed for Westpoint are firmly fixed and are retained through successive generations of asexual reproduction.

Westpoint has not been observed under all possible environmental conditions. The phenotype may vary significantly with variations in environment such as temperature, light intensity, and daylength. The following observations, measurements, and comparisons describe plants grown in a field in Barberton, Ohio and in Salinas, Calif. under conditions which are generally described in *Local Climatological Data, Annual Summary with Comparative Data, Akron, Ohio,* U.S. Department of Commerce, National Oceanic and Atmospheric Administration, Environmental Data Service, Washington, D.C. 1971, 1972, 1973, 1974, 1975, 1976, and *Local Climatological Data, Annual Summary with Comparative Data, Salinas, Calif.,* 1977 and 1978.

The following traits have been repeatedly observed and are determined to be basic characteristics of Westpoint which in combination distinguish this chrysanthemum as a new and distinct cultivar:

(1) Flat capitulum form.

(2) Pompon capitulum type (commercial double).

(3) Medium yellow ray floret color.

(4) Diameter across face of capitulum ranging from 25 to 40 mm.

(5) Short plant height (requiring 2–3 long day weeks prior to short days and 1 application of 2500 ppm B9-SP to attain a flowered plant height of 30 to 35 cm. in indoor flowering programs).

(6) Spreading branching pattern.

(7) Average natural season flowering date of September 28 (Ohio).

(8) Average flowering response period of 7 week in photoperiodic controlled flowering programs.

The accompanying color photographic drawings show typical inflorescence and foliage characteristics of Westpoint. Sheet 1 is a color photograph of Westpoint, and Sheet 2 of the photographic drawings shows Westpoint on the right and the comparison cultivar Nuggets, U.S. Plant Pat. No. 4,004, on the left. Some difficulty was encountered in obtaining accurate color representation, with the photographic drawings showing the inflorescence of Westpoint as more golden, or less yellow than the actual flower color of Westpoint. The color readings within the following descriptions are, however, correct.

Of the many commercially available cultivars known to the present inventors, the most similar existing cultivar in comparison to Westpoint is Nuggets. Sheet 2 of the photographic drawings compares Westpoint and Nuggets, and Chart A contains a comparison of certain characteristics of Westpoint with the same characteristics of Nuggets. It will be noted that in comparison to Nuggets, Westpoint has lighter yellow ray floret color, earlier natural season flowering date, shorter plant height, more spreading branching pattern, and smaller diameter across face of capitulum. The capitulum form and capitulum type of Westpoint are similar to those same characteristics of Nuggets.

In the following description, color references are made to A Limit Color Cascade, Munsell Company, 1972 edition. The color values were determined between 8:00 and 8:30 A.M. on Sept. 12, 1978 under 100 foot-candle light intensity at Salinas, Calif.

Botanical classification: *Chrysanthemum morifolium,* Ramat., cv Westpoint.

I. INFLORESCENCE

A. Capitulum:

*Form.*—Flat.

*Type.*—Pompon (commercial double).

*Permanence.*—14–21 days.

*Diameter across face.*—25 to 40 mm.

B. Corolla of ray florets:

*Color (abaxial).*—26-6 to 26-5 (immature) to 26-4 to 26-3 (mature).

*Color (adaxial).*—26-4 to 26-3.

C. Reproductive organs:

*Androecium.*—Present disc florets; scant pollen.

*Gynoecium.*—Present both ray and disc florets.

II. PLANT

A. General appearance: Spreading branching pattern; short height.

B. Foliage:

*Color (abaxial).*—Approximately 20-14 to 20-13.

*Color (adaxial).*—Approximately 21-14 overlaid with white.

Chart A

Comparison Of Westpoint And Nuggets.

| Cultivar | Ray Floret Color | Capitulum Form And Type | Average Natural Season Flower Date (Ohio) | Plant Height | Branching Pattern And Spread | Diameter Across Face Of Capitulum |
|---|---|---|---|---|---|---|
| Westpoint | Medium yellow | Flat pompon | September 28 | Short, from 20 to 25 cm. | Spreading, from 30 to 35 cm. | 25 to 40 mm. |
| Nuggets | Golden yellow | Flat pompon | September 28 | Medium, from 30 to 35 cm. | Semi-spreading, from 25 to 30 cm. | 30 to 40 mm. |

Comparisons Made Of Plants Grown Under Natural Season Outdoor Field Conditions In Barberton, Ohio And In Salinas, California.

We claim:

1. A new and distinct cultivar of *Chrysanthemum morifolium,* Ramat., plant known by the name Westpoint and particularly characterized as to uniqueness by the combined characteristics of flat capitulum form, pompon capitulum type (commercial double), medium yellow ray floret color, diameter across face of capitulum up to 40 mm., short plant height, spreading branching pattern, average natural season flowering date of September 28, and average flowering response period of seven weeks in photoperiodic controlled short day programs.

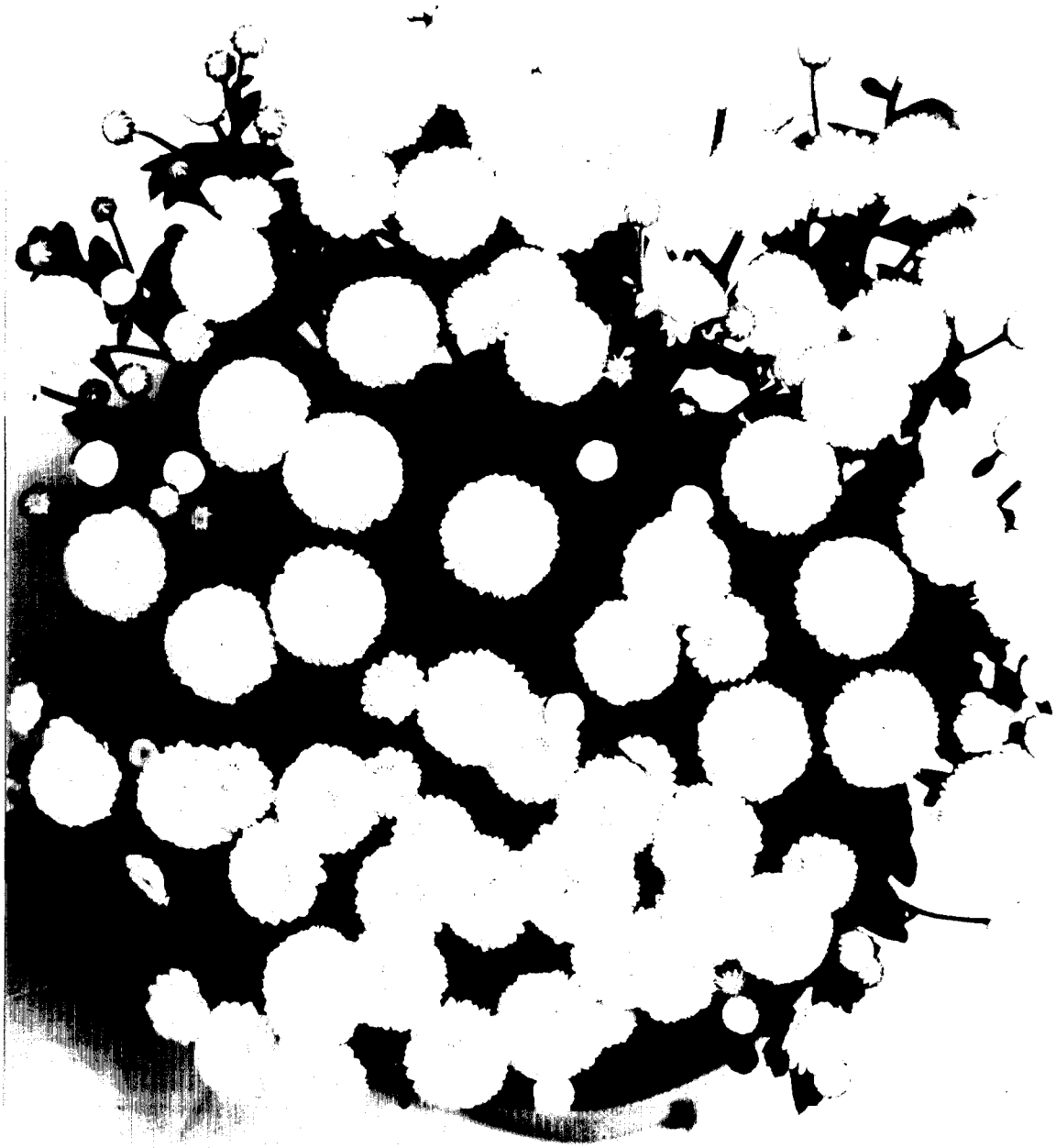

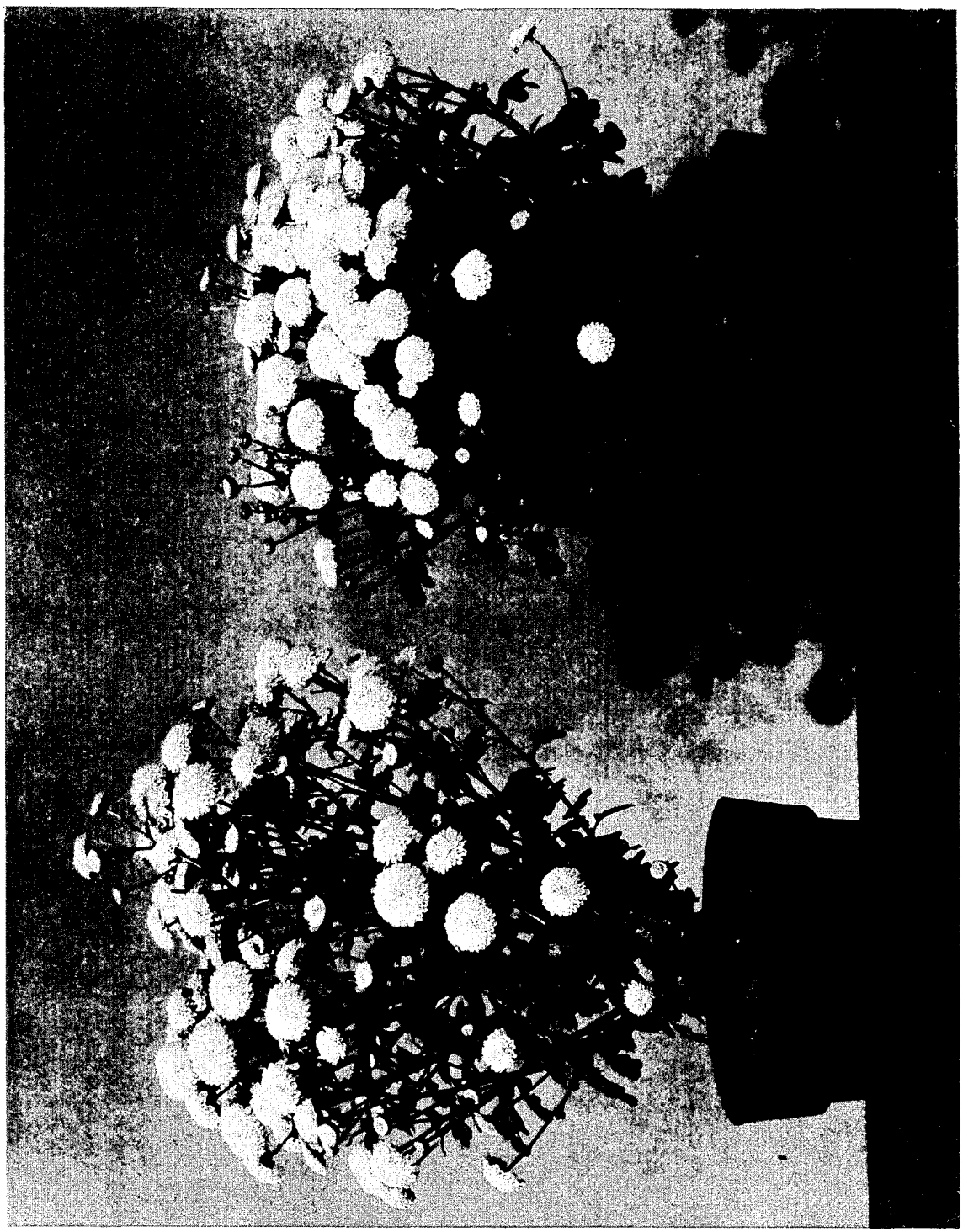

* * * * *